United States Patent [19]

Ikushima et al.

[11] 4,248,867
[45] Feb. 3, 1981

[54] STABILIZED OILY PREPARATION OF 1α-HYDROXY-VITAMIN D AND METHOD FOR MANUFACTURING THE SAME

[75] Inventors: Heizi Ikushima, Kawaguchi; Kazuo Igusa, Tokorozawa; Sadao Bessho, Tokyo, all of Japan

[73] Assignee: Chugai Seiyaku Kabushiki Kaisha, Tokyo, Japan

[21] Appl. No.: 915,987

[22] Filed: Jun. 14, 1978

[30] Foreign Application Priority Data

Sep. 29, 1977 [JP] Japan .................. 52/116054

[51] Int. Cl.³ .............................................. A61K 31/59
[52] U.S. Cl. ............................. 424/236; 424/238; 260/397.2
[58] Field of Search ........................ 424/236, 238; 260/397.2

[56] References Cited

U.S. PATENT DOCUMENTS

| | | | |
|---|---|---|---|
| 3,149,037 | 9/1964 | Aiello et al. | 424/236 |
| 3,901,928 | 8/1975 | Hesse et al. | 260/397.2 |

FOREIGN PATENT DOCUMENTS

| | | | |
|---|---|---|---|
| 2348697 | 4/1978 | France | 260/397.2 |
| 52-128210 | 10/1977 | Japan | 260/397.2 |
| 52-130905 | 11/1977 | Japan | 260/397.2 |
| 53-12414 | 2/1978 | Japan | 260/397.2 |

Primary Examiner—Elbert L. Roberts
Attorney, Agent, or Firm—Browdy and Neimark

[57] ABSTRACT

A stabilized oily preparation of a 1α-hydroxy-vitamin D for oral administration comprising a 1α-hydroxy-vitamin D and, as oily diluent, a triglyceride of saturated middle chain fatty acid which has been treated under certain conditions, and a method for manufacturing the same are disclosed.

8 Claims, 1 Drawing Figure

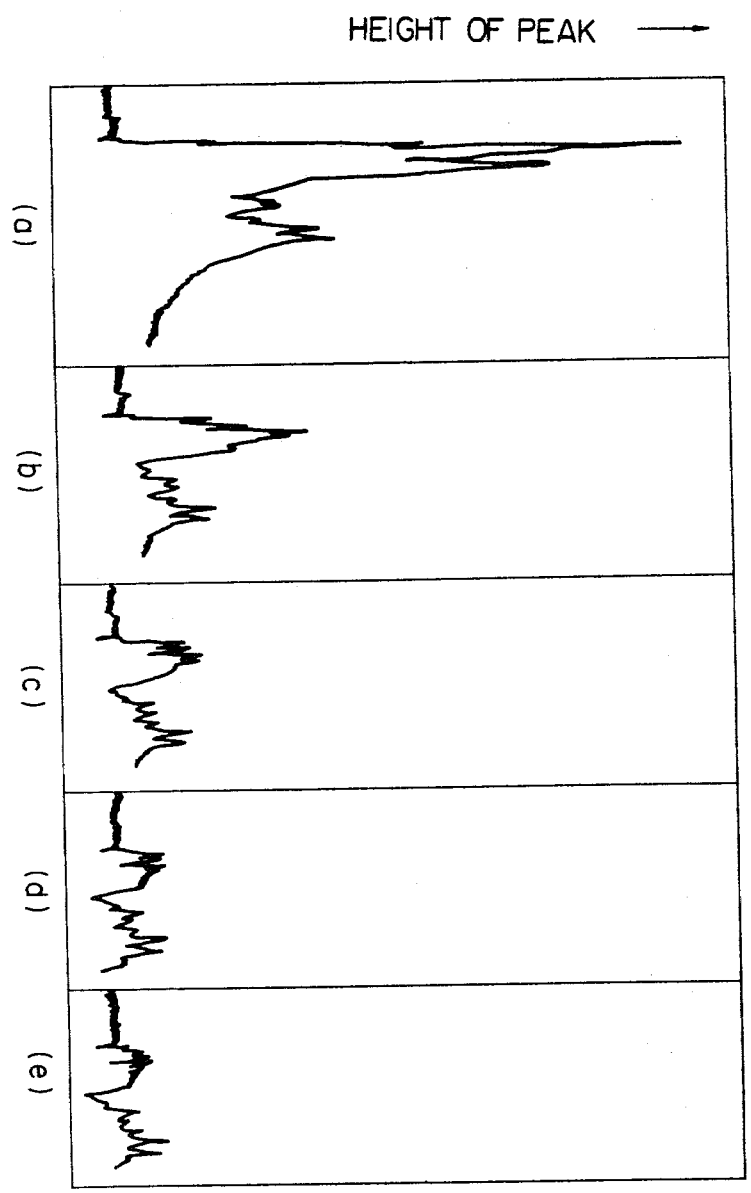

STABILIZED OILY PREPARATION OF 1α-HYDROXY-VITAMIN D AND METHOD FOR MANUFACTURING THE SAME

This invention relates to a stabilized preparation containing a 1α-hydroxy-vitamin D for oral administration and a method for manufacturing the same.

In recent years, various vitamin Ds which have hydroxyl radicals at 1α-position have been given attention due to their strong bioactivity. Such vitamins have unusually strong bioactivity and are used in a very small dose, so a uniform dispersion of the vitamin in a preparation is required, and for ease in preparing a uniform dispersion, a method of manufacturing a preparation by dissolving a 1α-hydroxy-vitamin D in an oily diluent has been desired. Further, if the oily preparation is encapsulated in soft gelatin capsules, oral administration of the preparation becomes more convenient. However, since 1α-hydroxy-vitamin D is usually used in a very small dose, and the amount of oily diluent which is used is $10^4$–$10^5$ times that of 1α-hydroxy-vitamin D, the stability of the 1α-hydroxy-vitamin D is seriously influenced by the oily diluent. Thus, the bioactivity is significantly reduced if an unsuitable oily diluent is selected.

Further, 1α-hydroxy-vitamin D is very sensitive to exposure to light, particularly to ultraviolet light and, therefore, its handling or treatment should be effected very carefully. Particularly, the preparation of the oily solution of a 1α-hydroxy-vitamin D and its encapsulation should be effected under light-intercepted conditions. In addition, since the resulting oily solution and capsules are also sensitive to exposure to visible light, they need to be stored or transported under cool and dark conditions and, therefore, the handling is very complicated.

The inventors of this invention searched for a way of preparing a stable pharmaceutical preparation containing a 1α-hydroxy-vitamin D, giving emphasis to selection of suitable oily diluents. They found that a triglyceride of fatty acid, especially triglyceride of saturated middle chain fatty acid(s) (referred to as MCT hereinafter) is suitable, because 1α-hydroxy-vitamin D is easily dispersed in such triglyceride and also it is easily and quickly absorbed in the intestinal tract. It was found that a pharmaceutical preparation which is manufactured by dissolving a 1α-hydroxy-vitamin D in an MCT, encapsulating the solution in soft gelatin capsules and wrapping the capsule preparation with a transparent plastic film capable of intercepting ultraviolet light in a conventional manner is stable under exposure to ultraviolet light and is easily and quickly absorbed in the intestinal tract.

However, such preparation was unstable under exposure to visible light. One reason is because commercially available MCT is derived from natural material and, therefore, certain substances which adversely influence the stability of a 1α-hydroxy-vitamin D are present in trace amounts and can not be completely removed by the usual separation or purification processes. The inventors tried to purify a commercially available MCT by several distillation and decoloration steps. However, an oily preparation containing a 1α-hydroxy-vitamin D prepared by the use of the MCT purified as above was still unstable under exposure to visible light and became inactive with the passage of time.

The inventors of this invention continued their research to find the surprising fact that a very stable oily preparation of a 1α-hydroxy-vitamin D can be obtained by dissolving the vitamin in MCT which has previously been irradiated with ultraviolet light. Further, the inventors found from their study of a high performance liquid chromatogram of MCT that the irradiation with ultraviolet light causes certain characteristic variation of peak(s) and that there is significant correlation between the variation of the peak(s) and the stability of a 1α-hydroxy-vitamin D in the irradiated MCT. They continued their study based on this discovery to complete this invention.

This invention relates to a stable oily preparation of a 1α-hydroxy-vitamin D for oral administration which comprises a 1α-hydroxy-vitamin D and, as oily diluent, an MCT which has been irradiated with ultraviolet light and which has peak(s) detected at a retention time around 2 minutes 50 seconds, as measured with a high performance liquid chromatography in the manner described in (a) and (b) of Experiment 2 hereunder, with said peak(s) being less than that given by the same measurement as above using $1.5 \times 10^{-10}$ M of ethyl aminobenzoate, as an internal standard substance. Also, this invention relates to a method for preparing a stable oily preparation containing a 1α-hydroxy-vitamin D.

The stable oily preparation according to this invention may be prepared, for example, by irradiating a saturated MCT with ultraviolet light and dissolving a 1α-hydroxy-vitamin D in the MCT by a conventional way.

Light sources which can be used in this invention include any light source emitting light having wavelength longer than 290 nm, such as sunlight, xenon lamp, mercury lamp and fluorescent lamp. The irradiation time may vary within the term of from several tens of minutes to several tens of hours, preferably from 1 to 60 hours depend on the type of light source and the strength of light. If an MCT is purged with an inert gas to remove oxygen dissolved in the MCT and then irradiated, a desired MCT can be obtained within a short period of time, although MCT almost equivalent to that above can be obtained by long irradiation even if oxygen is not purged.

A 1α-hydroxy-vitamin D used herein means a vitamin D having a hydroxyl group at 1α-position which includes, for example, 1α-hydroxy-vitamin $D_3$, 1α,25-dihydroxy-vitamin $D_3$, 1α,24-dihydroxy-vitamin $D_3$, 1α,24,25-trihydroxy-vitamin $D_3$ and the like.

A saturated middle chain triglyceride (MCT) means a triglyceride of saturated $C_6$–$C_{12}$ middle chain fatty acid and is liquid at room temperature under atmospheric pressure.

The drawing shows high performance liquid chromatograms of a commercially available MCT and MCT irradiated with ultraviolet light according to this invention.

In the chart (a), a commercially available saturated MCT is chromatographed. In the charts (b), (c), (d) and (e), a commercially available MCT is purged with helium gas, irradiated with xenon lamp (1.5 KW) for 2, 8, 24 and 48 hours, respectively, and then chromatographed.

This invention is further illustrated by the following Experiments and Example, but they must not be construed as limiting this invention.

EXPERIMENT 1

In this Experiment, the difference between components of a commercially available MCT and those of a light-irradiated MCT was confirmed by analysis with a high performance liquid chromatography.

The MCT sold by The Nisshin Oil Mills Ltd., Japan under the name of ODO was used for this experiment. Colorless transparent glass ampoules each having 50 ml capacity were filled with 50 ml of the MCT, purged with helium at a flow rate of 150 ml/min. for one minute and sealed. The ampoules were irradiated with xenon lamp (1.5 KW) for 2, 8, 24 or 48 hours.

The commercially available ODO and each of the irradiated ODO were analyzed under the following conditions using the high performance liquid chromatograph Model ALP/GDC sold by Nihon Waters Ltd., Japan.

Analytical Conditions:
Packing: $\mu$ Bondapak FAA
Mobile Phase: methanol-distilled water (9:1)
Flow Rate: 1 ml/min
Detector: U.V. photometer (313 nm)
Detection Sensitivity: 0.01
Recorder Sensitivity: 5 mV FS
Sample Amount: 10 $\mu$l The results are shown in the drawing. As shown in the drawing, there is a high correlation between the irradiation time and height of peak revealed as a retention time ranging from 3 to 6 minutes.

EXPERIMENT 2

Since several peaks were revealed around the questioned retention time, under the conditions of Experiment 1, it was difficult to precisely calculate the area of the peaks. Accordingly, in this Experiment, the MCT samples prepared as in Experiment 1 were analyzed by the same equipment using the following conditions. The height of the peak revealed at a retention time of around 2 minutes 50 seconds correlated closely with the stability of a 1$\alpha$-hydroxy-vitamin D dissolved in the corresponding MCT.

(a) Analysis Conditions:
Packing: $\mu$ Porasil
Mobile Phase: chloroform for liquid chromatography-acetonitrile for liquid chromatography (8:2)
Flow Rate: 1 ml/min
Detector: U.V. photometer (254 nm)
Detection Sensitivity: 0.02

(b) Analytical Method:
MCT was precisely measured and correctly diluted with the same solvent as used in the mobile phase for the chromatography to give samples each containing 0.3 $\mu$g of MCT.

The results are shown in the Table below.

In order to avoid the analytical errors caused by a particular analyzer, mobile phase, ambient conditions under which analysis is effected or the like, the height of peak shown in the table was evaluated in terms of moles of ethyl aminobenzoate, the internal standard substance, the height of peak of which is equal to the height of MCT. The ethyl aminobenzoate used was of the grade defined in Pharmacopoeia of Japan, 9th Edition.

In the table, the residual ratio was defined as follows. Each of the capsule preparations containing 1$\alpha$-hydroxy-vitamin D$_3$ prepared as in Example hereunder was placed under accelerative condition by heating it in a constant temperature bath at 40° C. for 60 days and, after wrapping the capsule with ultraviolet light-intercepting transparent film, exposed to a fluorescent lamp of 500 luxes for 600 hours. The thus treated sample was assayed in terms of the residual amount of 1$\alpha$-hydroxy-vitamin D$_3$ and the amount was shown as a ratio assuming that the amount of 1$\alpha$-hydroxy-vitamin D$_3$ in the untreated sample is 100.

TABLE

| Runs | Irradiation Time | Height of Peak | Residual Ratio (%) 40° C. 60 days | Residual Ratio (%) 500 luxes 600 hours |
|---|---|---|---|---|
| 1 | 0 (commercial A) | $4.2 \times 10^{-10}$ | 64.2 | 42.3 |
| 2 | 0 (commercial B) | $2.8 \times 10^{-10}$ | 84.0 | 75.6 |
| 3 | 0 (commercial C) | $3.4 \times 10^{-10}$ | 77.3 | 62.7 |
| 4 | 12 hours | $1.4 \times 10^{-10}$ | 95.2 | 93.5 |
| 5 | 24 hours | $9.6 \times 10^{-11}$ | 97.4 | 96.6 |
| 6 | 48 hours | $3.2 \times 10^{-11}$ | 99.7 | 98.7 |

As shown in the Table, a very high correlation between the height of peak on the MCT and the stability of 1$\alpha$-hydroxy-vitamin D$_3$ in the pharmaceutical preparation was clearly observed. That is, as the height of peak was lowered (molar concentration of ethyl aminobenzoate were reduced), the stability of the 1$\alpha$-hydroxy-vitamin D dissolved in the corresponding MCT improved. The results in the Table also showed that each of the commercially available MCTs gave a value of more than $2.5 \times 10^{-10}$ M and had only poor ability for stabilizing the 1$\alpha$-hydroxy-vitamin D, while the MCT exposed to ultraviolet light for a period longer than a certain length had a value less than $1.5 \times 10^{-10}$ M and the preparation of the 1$\alpha$-hydroxy-vitamin D in the treated MCT showed significantly improved stability.

EXAMPLE

1$\alpha$-Hydroxy-vitamin D$_3$ was dissolved in each of the commercially available MCT which corresponded to MCTs in Runs 1-3 in the Table above and the solution was charged in transparent soft gelatin capsules in an amount of 1 $\mu$g of 1$\alpha$-hydroxy-vitamin D$_3$ per capsule in a conventional manner to give capsule preparations.

Separately, the commercially available MCT in Run 3 above (50 ml) was put in a colorless glass ampoule, purged with helium gas at a flow rate of 150 ml/min for 1 minute and, after sealing, irradiated with xenon lamp (1.5 KW) for 12, 24 or 48 hours. The thus treated MCT was used to give soft gelatin capsule preparations (Runs 4-6) in the same manner as for Runs 1-3.

We claim:
1. A method for manufacturing a stabilized oily preparation which comprises irradiating a triglyceride of saturated middle chain fatty acid(s) with light longer than 290 nm, and dissolving a 1$\alpha$-hydroxy-vitamin D in the treated triglyceride.

2. A method according to claim 1 wherein a light source of said light is selected from the group consisting of sunlight, xenon lamp, mercury lamp and fluorescent lamp.

3. A method according to claim 1 wherein said irradiation is effected for 1-60 hours.

4. A method according to claim 1 wherein said irradiating step takes place with said saturated middle chain fatty acid(s) under an inert atmosphere.

5. A method in accordance with claim 1 wherein said triglyceride is a triglyceride of saturated $C_6$-$C_{12}$ middle chain fatty acid(s) and is liquid at room temperature under atmospheric pressure.

6. A method in accordance with claim 1, wherein said 1α-hydroxy-vitamin D is selected from the group consisting of 1α-hydroxy-vitamin $D_3$, 1α,25-dihydroxy-vitamin $D_3$, 1α,24-dihydroxy-vitamin $D_3$ and 1α,24,25-trihydroxy-vitamin $D_3$.

7. A method in accordance with claim 5, wherein said 1α-hydroxy-vitamin D is selected from the group consisting of 1α-hydroxy-vitamin $D_3$, 1α,25-dihydroxy-vitamin $D_3$, 1α,24-dihydroxy-vitamin $D_3$ and 1,24,25-trihydroxy-vitamin $D_3$.

8. A stabilized oily preparation produced in accordance with the process of claims 1, 2, 3, 4, 5, 6 or 7.

* * * * *